United States Patent [19]

Eidenschink et al.

[11] Patent Number: 5,180,521
[45] Date of Patent: Jan. 19, 1993

[54] CHIRAL COMPOUNDS

[75] Inventors: Rudolf Eidenschink, Mühltal; Reinhard Hopf, Heringen; Eike Poetsch, Mühltal, all of Fed. Rep. of Germany

[73] Assignee: Merck Patent Gesellschaft mit beschraenkter Haftung, Darmstadt, Fed. Rep. of Germany

[21] Appl. No.: 545,666

[22] PCT Filed: Jan. 31, 1987

[86] PCT No.: PCT/DE87/00037

§ 371 Date: Oct. 16, 1987

§ 102(e) Date: Oct. 16, 1987

[87] PCT Pub. No.: WO87/05015

PCT Pub. Date: Aug. 27, 1987

Related U.S. Application Data

[63] Continuation-in-part of Ser. No. 116,756, Oct. 16, 1987, abandoned.

[30] Foreign Application Priority Data

Feb. 17, 1986 [DE] Fed. Rep. of Germany ....... 3604905

[51] Int. Cl.$^5$ .................... C09K 19/34; C07D 211/72; C07D 239/00; C07C 255/00
[52] U.S. Cl. ................... 252/299.61; 252/299.63; 558/426; 558/431; 546/275; 546/276; 546/290; 546/296; 546/300; 544/242; 544/316; 544/335; 544/336; 544/357; 544/239; 544/224; 544/238
[58] Field of Search ....................... 252/299.63, 299.01, 252/299.61; 558/426, 431; 546/275, 276, 290, 296, 300; 544/242, 316, 335, 336, 357, 239, 224, 238, 239

[56] References Cited

U.S. PATENT DOCUMENTS

| 4,406,814 | 9/1983 | Ferrato | 252/299.63 |
|---|---|---|---|
| 4,510,069 | 4/1985 | Eidenschink et al. | 252/299.61 |
| 4,629,581 | 12/1986 | Petrzilka et al. | 252/299.63 |
| 4,659,499 | 4/1987 | Ferrato | 252/299.63 |
| 4,663,073 | 5/1987 | Sucrow et al. | 252/299.63 |
| 4,707,295 | 11/1987 | Pohl et al. | 252/299.63 |
| 4,726,911 | 2/1988 | Krause et al. | 252/299.61 |
| 4,753,752 | 6/1988 | Raynes et al. | 252/299.63 |
| 4,764,619 | 8/1988 | Gunjima et al. | 252/299.63 |
| 4,834,904 | 5/1989 | Krause et al. | 252/299.01 |
| 4,846,998 | 7/1989 | Pohl et al. | 252/299.63 |
| 4,986,931 | 1/1991 | Eidenschink et al. | 252/299.63 |
| 5,089,168 | 2/1992 | Krause et al. | 252/299.61 |

FOREIGN PATENT DOCUMENTS

| 3221941 | 12/1983 | Fed. Rep. of Germany | 252/299.63 |
|---|---|---|---|
| 3510432 | 9/1986 | Fed. Rep. of Germany | 252/299.61 |
| 3533333 | 3/1987 | Fed. Rep. of Germany . | |
| 56-92836 | 7/1981 | Japan | 252/299.63 |
| 57-40581 | 3/1982 | Japan | 252/299.63 |
| 61-10544 | 1/1986 | Japan . | |
| 61-236743 | 10/1986 | Japan | 252/299.63 |
| 86/04328 | 7/1986 | World Int. Prop. O. | 252/299.63 |
| 87/1717 | 3/1987 | World Int. Prop. O. . | |
| 88/4290 | 6/1988 | World Int. Prop. O. . | |

Primary Examiner—Robert L. Stoll
Assistant Examiner—Philip Tucker
Attorney, Agent, or Firm—Millen, White, Zelano and Branigan

[57] ABSTRACT

Optically active compounds of the formula I can be used as components of chiral tilted smectic liquid crystal phases.

20 Claims, No Drawings

CHIRAL COMPOUNDS

This application is a continuation-in-part of application Ser. No. 07/116,756, filed Oct. 16, 1987, now abandoned.

The invention relates to optically active compounds of the formula I $$R^1-A^1-Z^1-A^2-R^2 \qquad I$$

wherein $R^1-A^1-A^1$ is $R^1-A-Z^1$, $R^1-A^4-A-Z^1$ or $R^1-A-A^4-Z^1$ $R^1$ and $R^2$ are each H, an alkyl group with 1-12 C atoms, wherein one or two non-adjacent $CH_2$—groups can also be replaced by O atoms and/or —CO—groups and/or —CO—O—groups and/or —CH=CH— groups and/or —CH halogen— and/or —CHCN— groups, F, Cl, Br, Cn or $R^3-A^3-Z^2$, is a 1,4-cyclohexylene or 1,4-cyclohexenylene group, wherein one or two non-adjacent $CH_2$ groups can also be replaced by —O— and/or —S—, which is substituted in the 2-, 3-, 5- or 6-position by hydroxyl, halogen, nitrile and/or an alkyl group or a fluorinated alkyl group with in each case 1-10 C atoms, wherein one or two non-adjacent $CH_2$ groups can also be replaced by —O—, —CO—, —O—CO—, —CO—O— and/or —CH=CH—, and which can optionally also be substituted in the 1- and/or 4-position by hydroxyl, halogen, nitrile and/or in alkyl group or a fluorinated alkyl group with in each case 1-4 C atoms, wherein one or two nonadjacent $CH_2$ groups can also be replaced by —O—, —CO—, —O—CO—, —CO—O— and/or —CH=CH—, $A^2$, $A^3$ and $A^4$ are each 1,4 -phenylene which is unsubstituted or substituted by one or two F and/or Cl atoms and/or $CH_3$- groups and/or CN- groups, wherein one or two CH groups can also be replaced by N, 1,4-cyclohexylene, wherein one or two non-adjacent $CH_2$ groups can be replaced by O atoms and/or S atoms, piperidine- 1,4-diyl, 1,4-bicyclo(2,2,2)-octylene, decahydronaphthalene-2,6-diyl or 1,2,3,4-tetrahydronaphthalene-2,6-diyl groups, $Z^1$ and $Z^2$ are each —CO—O—, —O—CO—, —$CH_2CH_2$—, —$OCH_2$—, —$CH_2O$— or a single bond and $R^3$ is H, an alkyl group with 1-12 C atoms, wherein one or two non-adjacent $CH_2$ groups can also be replaced by O atoms and/or —CO— groups and/or —CO—O—groups and/or —CH=CH-groups, F, Cl, Br or Cn.

Like similar compounds described in German Offenlegungsschrift 3,515,373, the compounds of the formula I can be used as components of chiral tilted smectic liquid crystal phases.

Chiral tilted smectic liquid crystal phases with ferroelectric properties can be prepared by adding a suitable chiral doping substance to base mixtures containing one or more tilted smectic phases (L. A. Beresnev et al., Mol. Cryst. Liq. Cryst. 89, 327 (1982); and H. R. Brand et al., J. Physique 44, (lett.), L-771 (1983)). Such phases can be used as dielectrics for rapid-switching displays based on the principle of SSFLC technology described by Clark and Lagerwall (N. A. Clark and S. T. Lagerwall, Appl. Phys. Lett. 36, 899 (1980); and U.S. Pat. No. 4,366,924) on the basis of the ferroelectric properties of the chiral titled phase. The elongated molecules are arranged in layers in this phase, the molecules having an angle of tilt to the layer perpendicular. On progressing from layer to layer, the direction of tilt changes by a small angle with respect to an axis perpendicular to the layers, so that a helical structure is formed. In displays based on the principle of SSFLC technology, the smectic layers are arranged vertically to the plates of the cell. The helical arrangement of the tilt directions of the molecules in suppressed by a very low distance between the plates (about 1-2 μm). This means that the longitudinal axes of the molecules are forced to align themselves in a plane parallel to the plates of the cell, whereupon two preferential tilt orientations are formed. By applying a suitable alternating electrical field, switching backwards and forwards between these two states can be effected in the liquid crystal phase which displays spontaneous polarization. This switching operation is considerably faster than in conventional twisted cells (TN-LCD's) based on nematic liquid crystals.

A great disadvantage for many applications of the materials with chiral tilted smectic phases (such as, for example, Sc*) currently available is that the dielectric anisotropy has values greater than zero or, if they are negative, values which differ only slightly from zero. Negative values of the dielectric anisotropy are necessary if the required planar orientation is to be effected by overlapping the control field with an AC holding field of low amplitude (J. M. Geary, SID conference, Orlando/Florida, April/May 1985, paper 8.3).

It has now been found that the use of compounds of the formula I as components of chiral tilted smectic mixtures can substantially reduce the disadvantages mentioned. The compounds of the formula I are thus outstandingly suitable as components of chiral tilted smectic liquid crystal phases. In particular, chiral tilted smectic liquid crystal phases which have a particularly high chemical stability and have favorable ferroelectric phase ranges, in particular wide Sc* phase range, negative or even positive dielectric anisotropy, low optical anisotropy, a favorable pitch height and spontaneous polarization values which are high for such phases can be prepared with the aid of these compounds. P is the spontaneous polarization in $nC/cm^2$.

By providing the compounds of the formula I, the range of liquid crystal substances which are suitable from various technological viewpoints for the preparation of ferroelectric mixtures is furthermore quite generally considerably widened.

The compounds of the formula I have a wide field of application. Depending on the choice of substituents, these compounds can be used as base materials from which liquid crystal phases are predominantly composed; however, it is also possible for compounds of the formula I to be added to liquid crystal base materials of other classes of compound, for example in order to vary the dielectric and/or optical anisotropy and/or the spontaneous polarization and/or the phase range and/or the angle of tilt and/or the pitch of such a phase. The compounds of the formula I are furthermore suitable as intermediates for the preparation of other substances which can be used as constituents of liquid crystal phases.

The compounds of the formula I are colorless in the pure state and have low values of optical anisotropy. The compounds of the formula I in some cases exhibit liquid crystal mesophases in a temperature range which is advantageously located for electrooptical use, but isotropic or monotropic liquid crystal compounds of the formula I can also advantageously be used as components of chiral tilted smectic phases. They are very stable to chemicals, heat and light.

The invention thus relates to the optically active compounds of the formula I and the use of the compounds of the formula I as components of liquid crystal phases.

The invention also relates to chiral tilted smectic liquid crystal phases containing at least one optically active compound of the formula I with at least one asymmetric carbon atom.

The invention furthermore relates to those phases with a content of at least one compound of the formula I and liquid crystal display elements, in particular electrooptical display elements, containing such phases.

For simplicity, in the following text pH is a 1,4-phenylene group, wherein one or two CH groups can also be replaced by N, Cy is a 1,4-cyclohexylene group, wherein one or two non-adjacent $CH_2$ groups can also be replaced by O atoms, and Bi is a bicyclo(2,2,2) octylene group.

Above and below, $R^1$, $R^2$, $R^3$, $A^1$, $A^2$, $A^3$, $A^4$, $A$, $Z^1$ and $Z^2$ have the meaning given, unless expressly indicated otherwise.

The compounds of the formula I accordingly include, in particular, compounds of the part formulae Ia and Ib (with two rings)

| | |
|---|---|
| $R^1\text{-A-}A^2\text{-}R^2$ | Ia |
| $R^1\text{-A-}Z^1\text{-}A^2\text{-}R^2$ | Ib |

Ie to Ik (with three rings)

| | |
|---|---|
| $R^1\text{-}A^4\text{-A-}A^2 R^2$ | Ie |
| $R^1\text{-A-}A^4\text{-}A^2\text{-}R^2$ | If |
| $R^1\text{-}A^4\text{-A-}Z^1\text{-}A^2\text{-}R^2$ | Ig |
| $R^1\text{-A-}A^4\text{-}Z^1\text{-}A^2\text{-}R^2$ | Ih |
| $R^1\text{-A-}Z^1\text{-}A^2\text{-}A^3\text{-}R^3$ | Ii |
| $R^3\text{-}A^3\text{-}Z^2\text{-A-}Z^1\text{-}A^2\text{-}R^2$ | Ij |
| $R^1\text{-A-}Z^1\text{-}A^2\text{-}Z^2\text{-}A^3\text{-}R^3$ | Ik |

Ip to Iaa (with four rings)

| | |
|---|---|
| $R^1\text{-}A^4\text{-A-}A^2\text{-}A^3\text{-}R^3$ | Ip |
| $R^1\text{-A-}A^4\text{-}A^2\text{-}A^3\text{-}R^3$ | Iq |
| $R^3\text{-}A^3\text{-}Z^2\text{-}A^4\text{-A-}A^2\text{-}R^2$ | Ir |
| $R^3\text{-}A^3\text{-}A^4\text{-A-}Z^1\text{-}A^2\text{-}R^2$ | Is |
| $R^1\text{-A-}A^4\text{-}A^2\text{-}Z^2\text{-}A^3\text{-}R^3$ | It |
| $R^1\text{-A-}A^4\text{-}Z^1\text{-}A^2\text{-}A^3\text{-}R^3$ | Iu |
| $R^1\text{-}A^4\text{-A-}Z^1\text{-}A^2\text{-}A^3\text{-}R^3$ | Iv |
| $R^1\text{-A-}A^4\text{-}Z^1\text{-}A^2\text{-}Z^2\text{-}A^3\text{-}R^3$ | Iw |
| $R^1\text{-}A^4\text{-A-}Z^1\text{-}A^2\text{-}Z^2\text{-}A^3\text{-}R^3$ | Ix |
| $R^3\text{-}A^3\text{-}Z^2\text{-}A^4\text{-A-}Z^1\text{-}A^2\text{-}R^2$ | Iy |
| $R^3\text{-}A^3\text{-}Z^2\text{-A-}A^4\text{-}Z^1\text{-}A^2\text{-}R^2$ | Iz |
| $R^3\text{-}A^3\text{-}Z^2\text{-A-}Z^1\text{-}A^2\text{-}Z^2\text{-}A^3\text{-}R^3$ | Iaa | and Iab to Iak (with five rings)

| | |
|---|---|
| $R^3\text{-}A^3\text{-}Z^2\text{-}A^4\text{-A-}Z^1\text{-}A^2\text{-}Z^2\text{-}A^3\text{-}R^3$ | Iab |
| $R^3\text{-}A^3\text{-}Z^2\text{-A-}A^4\text{-}Z^1\text{-}A^2\text{-}Z^2\text{-}A^3\text{-}R^3$ | Iac |
| $R^3\text{-}A^3\text{-}A^4\text{-A-}Z^1\text{-}A^2\text{-}Z^2\text{-}A^3\text{-}R^3$ | Iad |
| $R^3\text{-}A^3\text{-}Z^2\text{-}A^4\text{-A-}A^2\text{-}Z^2\text{-}A^3\text{-}R^3$ | Iae |
| $R^3\text{-}A^3\text{-}Z^2\text{-}A^4\text{-A-}Z^1\text{-}A^2\text{-}A^3\text{-}R^3$ | Iaf |
| $R^3\text{-}A^3\text{-A-}A^4\text{-}A^2\text{-}Z^2\text{-}A^3\text{-}R^3$ | Iag |
| $R^3\text{-}A^3\text{-}Z^2\text{-A-}A^4\text{-}A^2\text{-}A^3\text{-}R^3$ | Iah |
| $R^3\text{-}A^3\text{-}A^4\text{-A-}Z^1\text{-}A^2\text{-}A^3\text{-}R^3$ | Iai |
| $R^3\text{-}A^3\text{-}A^4\text{-A-}A^2\text{-}A^3\text{-}R^3$ | Iaj |
| $R^3\text{-}A^3\text{-A-}A^4\text{-}A^2\text{-}A^3\text{-}R^3$ | Iak |

Of these, those of the formulae Ia, Ib, Ie, If, Ig, Ih, Ii, Ip and Iq are particularly preferred.

The preferred compounds of the formula Ia include those of the part formulae Ia1 to Ia3:

| | |
|---|---|
| $R^1\text{-A-Ph-}R^2$ | Ia1 |
| $R^1\text{-A-Cy-}R^2$ | Ia2 |
| $R^1\text{-A-Bi-}R^2$ | Ia3 |

Of these, those of the part formulae Ia1 and Ia2 are particularly preferred.

The preferred compounds of the formula Ib include those of the part formulae Ib1 to Ib3:

| | |
|---|---|
| $R^1\text{-A-}Z^1\text{-Ph-}R^2$ | Ib1 |
| $R^1\text{-A-}Z^1\text{-Cy-}R^2$ | Ib2 |
| $R^1\text{-A-}Z^1\text{-Bi-}R^2$ | Ib3 |

Of these, those of the part formulae Ib1 and Ib2, especially those wherein $Z^1$ is —CO—O—, O—CO—or —$CH_2CH_2$—, are particularly preferred.

The preferred compounds of the formula Ie include those of the part formulae Ie1 and Ie2:

| | |
|---|---|
| $R^1\text{-Cy-A-Cy-}R^2$ | Ie1 |
| $R^1\text{-Cy-A-Ph-}R^2$ | Ie2 |

The preferred compounds of the formula If include those of the part formulae If1 to If4:

| | |
|---|---|
| $R^1\text{-A-Cy-Cy-}R^2$ | If1 |
| $R^1\text{-A-Ph-Ph-}R^2$ | If2 |
| $R^1\text{-A-Ph-Cy-}R^2$ | If3 |
| $R^1\text{-A-Cy-Ph-}R^2$ | If4 |

Of these, those of the part formulae If1 and If4 are particularly preferred.

The preferred compounds of the formula Ig include those of the part formulae Ig1 to Ig3:

| | |
|---|---|
| $R^1\text{-Cy-A-}Z^1\text{-Cy-}R^2$ | Ig1 |

R$^1$-Cy-A-Z$^1$-Ph-R$^2$      Ig2

R$^1$-Ph-A-Z$^1$-Cy-R$^2$      Ig3

Of these, those of the part formulae Ig1, in particular those wherein Z$^1$ is —CO—O—, —O—CO— or —CH$_2$CH$_2$—, are particularly preferred.

The preferred compounds of the formula Ih include those of the part formulae Ih1 to Ih4:

R$^1$-A-Cy-Z$^1$-Cy-R$^2$      Ih1

R$^1$-A-Ph-Z$^1$-Ph-R$^2$      Ih2

R$^1$-A-Ph-Z$^1$-Cy-R$^2$      Ih3

R$^1$-A-Cy-Z$^1$-Ph-R$^2$      Ih4

Of these, those of the part formulae Ih1, Ih2 and Ih3, especially those wherein Z$^1$ is —CO—O—, —O—CO— or —CH$_2$CH$_2$—, in particular —CO—O—, are particularly preferred.

The preferred compounds of the formula Ii include those of the part formulae Ii1 and Ii4:

R$^1$-A-Z$^1$-Cy-Cy-R$^3$      Ii1

R$^1$-A-Z$^1$-Ph-Cy-R$^2$      Ii2

R$^1$-A-Z$^1$-Cy-Ph-R$^2$      Ii3

R$^1$-A-Z$^1$-Ph-Ph-R$^2$      Ii4

Of these, those wherein Z$^1$ is —O—CO—, —CO—O— or —CH$_2$CH$_2$—, especially preferably —CH$_2$CH$_2$—, are particularly preferred.

The preferred compounds of the formula Ip include those of the part formulae Ip1 and Ip2:

R$^1$-Cy-A-Ph-Ph-R$^3$      Ip1

R$^1$-Cy-A-Ph-Cy-R$^3$      Ip2

The preferred compounds of the formula Iq include those of the part formulae Iq1 and Iq2:

R$^1$-A-Ph-Ph-Cy-R$^3$      Iq1

R$^1$-A-Ph-Cy-Cy-R$^3$      Iq2

In the compounds of the formulae above and below, R$^1$, R$^2$ and R$^3$ are preferably alkyl, or furthermore alkoxy or another oxaalkyl group.

Compounds of the formulae above and below wherein one of the radicals R$^1$, R$^2$ or R$^3$ is —CO—alkyl, —CO—O—alkyl, —OCO—alkyl or —OCOO—alkyl and the other is alkyl or alkoxy, are furthermore preferred.

In the preferred compounds of the formulae above and below, the alkyl radicals, in which one CH$_2$—group (alkoxy or oxaalkyl) can also be replaced by an O atom, can be straight-chain or branched. Preferably, they are straight-chain and have 5, 6, 7, 8, 9 or 10 C atoms, and are accordingly preferably pentyl, hexyl, heptyl, octyl, nonyl, decyl, pentoxy, hexoxy, heptoxy, octoxy, nonoxy or decoxy, and furthermore also ethyl, propyl, butyl, undecyl, dodecy, propoxy, ethoxy, butoxy undecoxy, dodecoxy, 2-oxapropyl (=2-methoxymethyl), 2- (=ethoxymethyl) or 3-oxabutyl (=2-methoxypentyl), 2,3- or 4-oxapentyl, 2-, 3-, 4- or 5-oxahexyl or 2-, 3-, 4-, 5- or 6-oxaheptyl.

A$^2$, A$^3$ and A$^4$ are preferably Cy or Ph. In the compounds of the formulae above and below, Ph is preferably a 1,4 -phenylene or a pyrimidine-2,5-diyl group, particularly preferably 1,4-phenylene. Cy is preferably a 1,4-cyclohexylene group.

Z$^1$ and Z$^2$ are preferably single bonds, and secondly, preferably, —O—CO—, —CO—O— or —CH$_2$CH$_2$ groups.

A is preferably a 1,4-cyclohexylene group which is substituted in the 2-, 3-, 5- or 6-position by hydroxyl, halogen, nitrile and/or an alkyl group with preferably 1-5 C atoms, wherein one or two non-adjacent CH$_2$ groups can also preferably be replaced by —O— and/or —CO—, and which can optionally also be substituted in the 1- and/or 4-position by halogen, nitrile and/or an alkyl group with 1-4 C atoms, in particularly by nitrile.

A is preferably a group selected from the formulae (A) to (C)

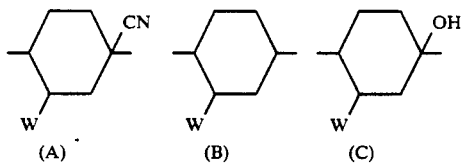

(A)      (B)      (C)

wherein W is OH, halogen, nitrile, alkyl, alkoxy, oxaalkyl, alkanoyl, alkanoyloxy or alkoxycarbonyl with in each case 1 to 10 C atoms.

Compounds of the formulae (A)–(C) wherein W is preferably alkyl, alkoxy, halogen or nitrile are furthermore preferred. W is particularly preferably CH$_3$.

A also includes the mirror images of the formulae (A) to (C).

R$^1$-A is furthermore preferably a group of the formulae (D)–(F)

(D)      (E)

(F)

wherein R$^4$ is preferably n-alkyl, n-alkoxy, n-alkoxycarbonyl carbonyl (in each case preferably with 1 to 10, in particular with 1 to 7, C atoms) or CN. R$^1$ here is H.

(D) and (F) in which R$^4$ is preferably CH$_3$ are particularly preferred.

The preferred meaning of W is F, Cl, CN, —CH$_3$ and —CH$_2$CH$_3$. Groups (A) and (B) are particularly preferred.

Z$^1$ is particularly preferably —CO—O, —O—CO— or —CH$_2$CH$_2$—, in particular the —CH$_2$CH$_2$—group.

Compounds of the formulae above and below with branched side chain groups R$^1$, R$^2$ or R$^3$ may occasionally be of importance because of a better solubility in the customary liquid crystal base materials. Branched groups of this type as a rule contain not more than one chain branching.

Preferred branched radicals are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-metnylpropoxy, 2-metnylbutoxy, 3-methylbutoxy, 2-methylpentoxy, 3-methylpentoxy, 2-ethylhexoxy, 1-methylhexoxy, 1-methylheptoxy, 2-oxa-3-methylbutyl and 3-oxa-4-methylpentyl.

Of the compounds of the formula I and Ia to Iq, those in which at least one of the radicals contained therein has one of the preferred meanings mentioned are preferred.

In the compounds of the above mentioned formulae, those stereoisomers in which the substituents $R^1$-, $R^1$-$A^4$-, $R^2$-$A^2$-$Z^1$- and $R^2$-$A^2$-$Z^1$-$A^4$- in the 1- and 4-position of ring A are in the trans-position and assume the equatorial position, whilst any additional substituent present in A in the 1- or 4-position assumes an axial position are preferred. These are as a rule more stable; in many cases, the cis-compounds (or mixtures) can be converted into the trans-compounds by treatment with a base, for example with K tert.-butylate, in an inert solvent, such as dimethyl sulfoxide.

The substituent W in the groups of the formulae (A) to (C) can assume equatorial or axial positions.

Those of the abovementioned formulae which contain one or more groups Dio, Dit, Pip and/or Pyr in each case include the two possible 2,5-position isomers (Dio, Dit, Pyr) or 1,4 -position isomers (Pip).

The compounds of the formula I are prepared by methods which are known per se, such as are described in the literature (for example in the standard works, such as Houben-Weyl, Methoden der Organischem Chemie (Methods of Organic Chemistry), Georg-Theieme-Verlag, Stuttgart), and in particular under reaction conditions which are known and suitable for the reactions mentioned. It is thereby also possible for variants which are known per se and are not mentioned here in more detail to be utilized.

If desired, the starting substances can also be formed in situ, such that they are not isolated from the reaction mixture but are immediately reacted further to give the compounds of the formula I.

Thus, the compounds of the formula I can be prepared by a procedure in which a compound which otherwise corresponds to the formula I but contains one or more reducible groups and/or C—C bonds instead of H atoms is reduced.

Preferred possible reducible groups are —CH=CH—groups, and furthermore, for example, free or esterified hydroxyl groups, aromatically bonded halogen atoms or carbonyl groups, Preferred starting substances for the reduction correspond to the formula I, but can contain a —CH=CH— group instead of a —CH$_2$CH$_2$- group and/or a —CO— groups instead of a —CH$_2$— group and/or a free or functionally modified (for example in the form of its p-toluenesulfonate) OH group instead of an H atom.

The reduction can be carried out, for example, by catalytic hydrogenation at temperatures between about 0° and about 200° under pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are advantageously nobel metals, such as Pt or Pd, which can be used in the form of oxides (for example PtO$_2$ or PdO) on a support (for example Pd-on-charcoal, calcium carbonate or strontium carbonate) or infinely divided form.

Ketones can also be reduced by the methods of Clemmensen (with zinc, zinc amalgam or tin and hydrochloric acid, advantageously in aqueous-alcoholic solution or in a heterogeneous phase system with water/toluene at temperatures between about 80° and 120°) or Wolff-Kishner (with hydrazine, advantageously in the presence of an alkali, such as KOH or NaOH, in a high-boiling solvent, such as diethylene glycol or triethylene glycol, at temperatures between about 100° and 200°), to give the corresponding compounds of the formula I containing alkyl groups and/or —CH$_2$CH$_2$—bridges.

Reductions with complex hydrides are furthermore possible. For example, arylsulfonyloxy groups can be removed by reduction with LiAlH$_4$, and in particular p-toluenesulfonyloxymethyl groups can be reduced to methyl groups, advantageously in an inert solvent, such as diethyl ether or THF, at temperatures between about 0 and 100°. Double bonds (also in the presence of CN groups!) can be hydrogenated with NaBH$_4$ or tributyltin hydride in methanol; thus, for example, the corresponding cyclohexane derivatives are formed from 1-cyanocyclohexene derivatives.

Esters of the formula I can also be obtained by esterification of corresponding carboxylic acids (or their reactive derivatives) with alcohols or phenols (or their reactive derivatives).

Particularly suitable reactive derivatives of the carboxylic acids mentioned are the acid halides, above all the chlorides and bromides, and furthermore the anhydrides, for example also mixed anhydrides, azides or esters, in particular alkyl esters with 1-4 C atoms in the alkyl group.

Particularly suitable reactive derivatives of the alcohols or phenols mentioned are the corresponding metal alcoholates or phenolates, preferably of an alkali metal, such as Na or K.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or phosphoric acid hexamethyltriamide, hydrocarbons, such as benzene, toluene or xylene, halogenohydrocarbons, such as carbon tetrachloride or tetrachloroethylene, and sulfoxides, such as dimethyl sulfoxide or sulfolane. Water-immiscible solvents can at the same time be advantageously used for azeotropic removal by distillation of the water formed during the esterification. An excess of an organic base, for example pyridine, quinoline or triethylamine, can occasionally also be used as the solvent for the esterification. The esterification can also be carried out in the presence of a solvent, for example by simply heating the components in the presence of sodium acetate. The reaction temperature is usually between −50° and +250°, preferably between −20° and +80°. At these temperatures, the esterification reactions are as a rule ended after 15 minutes to 48 hours.

In detail, the reaction conditions for the esterification largely depend on the nature of the starting substances used. Thus, a free carboxylic acid is as a rule reacted with a free alcohol or phenol in the presence of a strong acid, for example, a mineral acid, such as hydrochloric acid or sulfuric acid. A preferred reaction procedure is to react an acid anhydride or, in particular, an acid chloride with an alcohol, preferably in a basic medium, bases which are of importance being, in particular, alkali metal hydroxides, such as sodium or potassium hydroxide, alkali metal carbonates or bicarbonates, such as sodium carbonate, potassium carbonate or potassium bicarbonate, alkali metal acetates, such as sodium or potassium acetate, alkaline earth metal hydroxides, such as calcium hydroxide, or organic bases, such as triethylamine, pyridine, lutidine, collidine or quinoline. Another preferred embodiment of the esterification comprises a procedure in which the alcohol or phenol is first converted into the sodium alcoholate or phenolate or potassium alcoholate or phenolate, for example by treatment with ethanolic sodium hydroxide solution or potassium hydroxide solution, this alcoholate or phenolate is isolated and suspended in acetone or diethyl ether together with sodium bicarbonate or potassium carbonate, with stirring, and a solution of the acid chloride or anhydride in diethyl ether, acetone or DMF is added to this suspension, advantageously at temperatures between about $-25°$ and $+20°$.

Dioxane derivatives and dithiane derivatives of the formula I are advantageously prepared by reaction of a corresponding aldehyde (or one of its reactive derivatives) with a corresponding 1,3-diol or a corresponding 1,3-dithiol (or one of its reactive derivatives), preferably in the presence of an inert solvent, such as benzene or toluene, and/or a catalyst, for example a strong acid, such as sulfuric acid or benzene- or p-toluenesulfonic acid, at temperatures between 20° and about 150°, preferably between 80° and 120°. Suitable reactive derivatives of the starting substances are, above all, acetals.

The aldehydes and 1,3-diols or 1,3-dithiols mentioned and their reactive derivatives are known in some cases, and they can all be prepared without difficulty by standard processes of organic chemistry from compounds which are known from the literature. For example, the aldehydes are obtainable by oxidation of corresponding alcohols or by reduction of corresponding carboxylic acids or their derivatives, the diols are obtainable by reduction of corresponding diesters and the dithiols are obtainable by reaction of corresponding dihalides with NaSH.

To prepare nitriles of the formula I, corresponding acid amides, the for example those in which the radical X is replaced by a $CONH_2$ group, can be dehydrated. The amides are obtainable, for example, from corresponding esters or acids halides by reaction with ammonia. Examples of suitable dehydrating agents are inorganic acid chlorides, such as $SOCl_2$, $PCl_3$, $PCl_5$, $POCl_3$, $SO_2Cl_2$ and $COCl_2$, and furthermore $P_2O_5$, $P_2S_5$, $AlCl_3$ (for example as the double compound with NaCl), aromatic sulfonic acids and sulfonic acid halides. The reaction here can be carried out in the presence or absence of an inert solvent at temperatures between about 0° and 150°; possible solvents are, for example, bases, such as pyridine or triethylamine, aromatic hydrocarbons, such as benzene, toluene or xylene, or amides, such as DMF.

To prepare the abovementioned nitriles of the formula I, it is also possible for corresponding acid halides, preferably the chlorides, to be reacted with sulfamide, advantageously in an inert solvent, such as tetramethylene sulfone, at temperatures between about 80° and 150°, preferably at 120°. After customary working up, the nitriles can be isolated directly.

Ethers of the formula I are obtainable by etherification of corresponding hydroxy compounds, preferably corresponding phenols, the hydroxy compound advantageously first being converted into a corresponding metal derivative, for example into the corresponding alkali metal alcoholate or alkali metal phenolate by treatment with NaH, $NaNH_2$, NaOH, KOH, $Na_2CO_3$ or $K_2CO_3$. This alcoholate or phenolate can then be reacted with the corresponding alkyl halide or sulfonate or dialkyl sulfate, advantageously in an inert solvent, such as acetone, 1,2-dimethoxyethane, DMF or dimethyl sulfoxide, or an excess of aqueous or aqueous-alcoholic NaOH or KOH, at temperatures between about 20° and 100°.

Cyclohexanone derivatives of the formula I are furthermore accessible by acid-catalyzed rearrangement of the corresponding epoxides by processes which are known from the literature, for example by treatment with $BF_3$ etherate. The epoxides are obtainable by epoxidation of the corresponding cyclohexane derivatives by standard processes.

To prepare nitriles of the formula I, corresponding chlorine or bromine compounds of the formula I can also be reacted with a cyanide, advantageously with a metal cyanide, such as NaCn, KCn or $Cu_2(CN)_2$, for example in the presence of pyridine in an inert solvent, such as DMF or N-methylpyrrolidone, at temperatures between 20° and 200°.

The optically active compounds of the formula I are obtained by using corresponding optically active starting materials and/or by separation of the optical antipodes by means of chromatography by known methods.

The phases according to the invention preferably contain at least three, in particular at least five, compounds of the formula I. Chiral tilted smectic liquid crystal phases according to the invention of which the achiral base mixture contains, in addition to compounds of the formula I, at least one other component with a negative or relatively low positive dielectric anisotropy are particularly preferred. This/these other component(s) of the chiral base mixture can make up 1 to 50%, preferably 10 to 25%, of the base mixture. Suitable other components with a relatively low positive or a negative dielectric anisotropy are compounds of the part formulae Va to Vp:

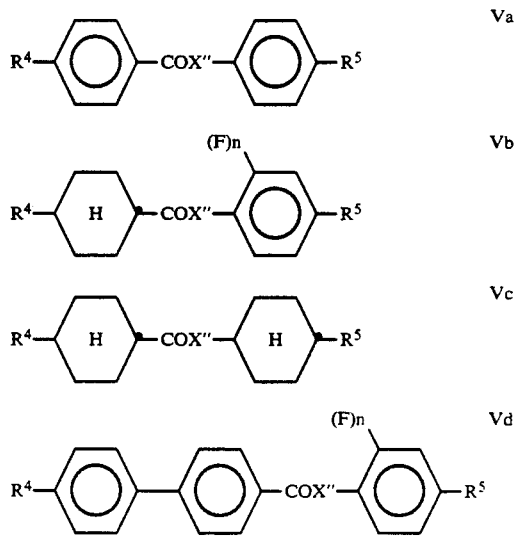

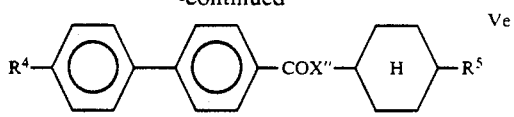

Ve

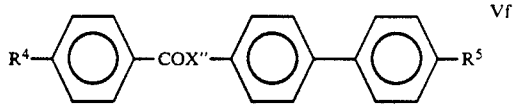

Vf

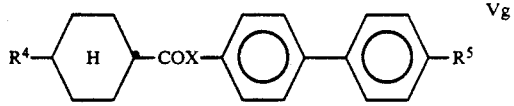

Vg

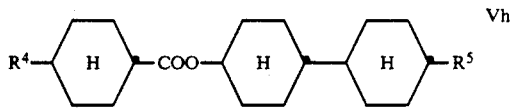

Vh

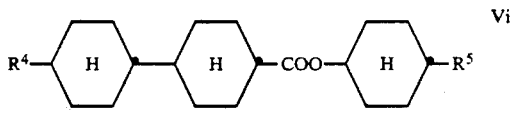

Vi

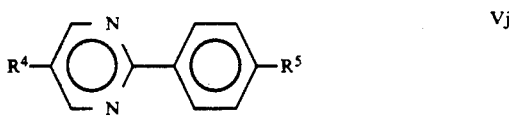

Vj

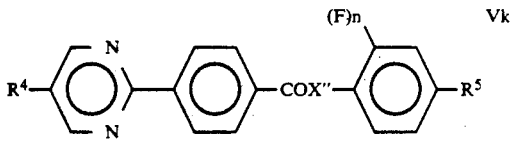

Vk

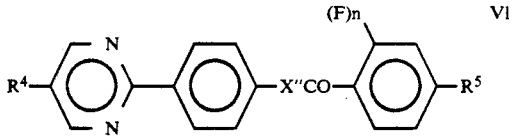

Vl

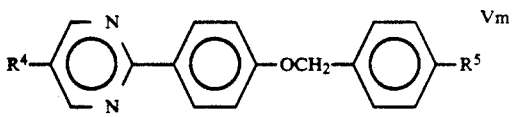

Vm

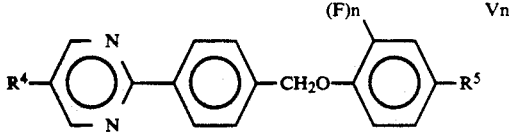

Vn

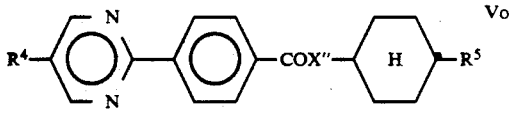

Vo

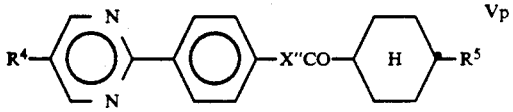

Vp $R^4$ and $R^5$ are each preferably straight-chain alkyl, alkoxy, alkanoyloxy or alkoxycarbonyl with in each case 3 to 12 C atoms. X" to O or S, preferably O. n is 0 or 1, The compounds of part formulae Va, Vb, Vd and Vf in which $R^4$ and $R^5$ are each straight-chain alkyl or alkoxy with in each case 5 to 10 C atoms are particularly preferred.

The compounds of the part formulae Vc, Vh and Vi are suitable as additives for reducing the melting point and are usually added to the base mixtures in an amount of not more than 5% preferably 1 to 3%. $R^4$ and $R^5$ in the compounds of the part formulae Vc, Vh and Vi are preferably straight-chain alkyl with 2 to 7, preferably 3 to 5, C atoms. Another class of compounds which is suitable for reducing the melting point in the phases according to the invention is that of the formula

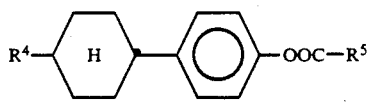

wherein $R^4$ and $R^5$ have the meaning given as preferred for Vc, Vh and Vi.

Compounds containing the structural element M, N or O

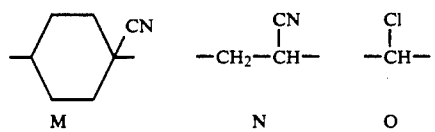

are furthermore suitable as other components with negative dielectric anisotropy.

Preferred compounds of this type correspond to the formulae VIb and VIc:

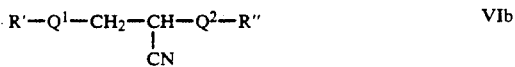 VIb

 VIc

R' and R" are each preferably straight-chain alkyl or alkoxy groups with in each case 2 to 10 C atoms. $Q^1$ and $Q^2$ each 1,4-phenylene, trans-1,4-cyclohexylene, 4,4'-biphenylyl, 4-(trans-4-cyclohexyl)-phenyl or trans,-trans-4,4'-bicyclohexyl, or one of the groups $Q^1$ and $Q^2$ is also a single bond.

$Q^3$ and $Q^4$ are each 1,4-phenylene, 4,4'-bi-phenylyl or trans-1,4-cycohexylene. One of the groups $Q^3$ and $Q^4$ can also be 1,4-phenylene wherein at least one CH-groups is replaced by N. R''' is an optically active radical with an asymmetric carbon atom of the structure

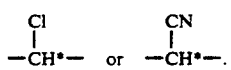

Particularly preferred compounds of the formula VIc are those of the formula VIc':

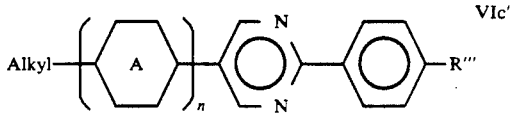 VIc' wherein A is 1,4-phenylene or trans-1,4-cyclohexylene and n is 0 or 1.

The compounds of the formula I are also suitable as components of nematic liquid crystal phases, for example for avoiding reverse twist.

These liquid crystal phases according to the invention consist of 2 to 25, preferably 3 to 15, components, at least one of which is a compound of the formula I. The other constituents are preferably chosen from the nematic or nematogenic substances, in particular the known substances, from the classes of azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-biscyclohexylbenzenes, 4,4'-bis-cyclohexylbiphenyls, phenyl- or cyclohexylpyrimidines, phenyl- or cyclohexylpyridazines and N-oxides thereof, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers, tolanes and substituted cinnamic acids.

The most important compounds which are suitable as constituents of such liquid crystal phases can be characterized by formula I'

R'-L-G-E-R"    I' wherein L and E are each a carbo- or heterocyclic ring system from the group formed by 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is

| —CH=CH— | —N(O)=N— |
| —CH=CY— | —CH=N(O)— |
| —C≡C— | —CH₂—CH₂— |
| —CO—O— | —CH₂—O— |
| —CO—S— | —CH₂—S— |
| —CH=N— | —COO—Phe—COO— | or a C—C single bond,

Y is halogen, preferably chlorine, or —Cn, and R' and R" are alkyl, alkoxy, alkanoyloxy, alkoxycarbonyl or alkoxycarbonyloxy with up to 18, preferably up to 8, carbon atoms, or one of these radicals is also CN, NC, NO₂, CF₃, F, Cl or Br.

In most of these compounds, R' and R" differ from one another, one of these radicals usually being an alkyl or alkoxy group. However, other variants of the envisaged substituents are customary. Many such substances or mixtures thereof are commercially available. All of these substances are obtainably by methods which are known from the literature.

The phases according to the invention contain about 0.1 to 99%, preferably 10 to 95% of one or more compounds of the formula I. Liquid crystal phases according to the invention containing 0.1–40%, preferably 0.5–30% of one or more compounds of the formula I are furthermore preferred.

The phases according to the invention are prepared in a manner which is customary per se. As a rule, the components are dissolved in one another, advantageously at elevated temperature.

The liquid crystal phases according to the invention can be modified by suitable additives such that they can be used in all the types of liquid crystal display elements disclosed to data.

Such additives are known to the expert and are described in detail in the literature. For example, it is possible to add conductive salts, preferably ethyldimethyl-dodecyl-ammonium 4-hexyloxybenzoate, tetrabutylammonium tetraphenylboranate or complex salts of crown ethers (compare, for example, I. Haller et al., Mol. Cryst. Liq. Cryst. Volume 24, pages 249–258 (1973)) to improve the conductivity, pleochroic dyes for the preparation of colored guest-host systems or substances for modifying the dielectric anisotropy, the viscosity and/or the orientation of the nematic phases.

Such substances are described, for example, in German Offenlegungsschriften 2,209,127, 2,240,864, 2,321,632, 2,338,281, 2,450,088, 2,637,430, 2,853,728 and 2,902,177.

The following examples are intended to illustrate the invention without limiting it. m.p.=melting point, c.p.=clear point. Percentage data above and below are percentages by weight; all the temperatures are given in degrees Celsius. "Customary working up" means: water is added, the mixture is extracted with methylene chloride, the organic phase is separated off, dried and evaporated and the product is purified by crystallization and/or chromatography.

The abbreviations used furthermore have the following meanings:

C: crystalline solid state, S: smectic phase (the index characterizes the type of phase), N: nematic state, Ch: cholesteric phase, I: isotropic phase. The figure between two symbols indicates the transition temperature in degrees Celsius.

EXAMPLE 1 a) 105 g of 2,4,6-triisopropylbenzenesulfonic acid hydrazide are added to a solution of 36 g of (+)-methylcyclohexanone in 630 ml of THF and the mixture is stirred at room temperature for 2 hours. Thereafter, 450 ml of methanol and 65 g of KCN are added and the mixture is heated under reflux for 2 hours. Customary working up and subsequent fractional distillation gives a mixture of the diastereomeric 3-methylcyclohexanecarbonitriles.

b) A lithium diisopropylamide solution (prepared from 140 ml of THF, 16 g of diisopropylamine and 100 ml of 1.6 molar butyllithium solution in hexane) is added to a solution of 17 g of 3-methylcyclohexanecarbonitrile in 140 ml of THF at −78°, 25 g of diethyl carbonate are added after 2 hours and the mixture is stirred for a further hour. After warming to room temperature and pouring onto 300 ml of ice-water, the mixture is neutralized with dilute hydrochloride acid. Customary working up and distillation give a mixture of the diastereomeric ethyl 3-methyl-1-cyanocyclhexanecarboxylates.

This ester is hydrolyzed by warming with ethanolic potassium hydroxide solution. Neutralization, extraction with methyl tert.-butyl ether and removal of the solvent by distillation give the mixture of the diastereomeric 1-cyano-3-methylcyclohexanecarboxylic acids.

c) A solution of 23 g of dicyclohexylcarbodiimide in 50 ml of CH₂Cl₂ is added to a mixture of 16 g of 1-cyano-3-methyl-cyclohexanecarboxylic acid, 25 g of 4'-hexyl-biphenyl-4-ol, 1.2 g of 4-diethylaminopyridine and 200 ml of methylene chloride at room temperature and the mixture is stirred for 2 hours. Customary working up and separation by column chromatography (silica gel/toluene) gives 4'-hexylbiphenyl-4-yl 1-cyano-3- methylcyclohexanecarboxylic as the pure product by recrystallization, m.p. 51°, $[\alpha]_D^{20} = +2.2°$.

The following compounds are prepared analogously:

4'-ethylbiphenyl-4-yl 1-cyano-3-methylcyclohexanecarboxylate
4'-propylbiphenyl-4-yl 1-cyano-3-methylcyclohexanecarboxylate
4'-butylbiphenyl-4-yl 1-cyano-3-methylcyclohexanecarboxylate
4'-pentylbiphenyl-4-yl 1-cyano-3-methylcyclohexanecarboxylate
4'-heptylbiphenyl-4-yl 1-cyano-3-methylcyclohexanecarboxylate
4'-ethoxybiphenyl-4-yl 1-cyano-3-methylcyclohexanecarboxylate
4'-propoxybiphenyl-4-yl 1-cyano-3-methylcyclohexanecarboxylate
4'-butoxybiphenyl-4-yl 1-cyano-3-methylcyclohexanecarboxylate
4'-pentoxybiphenyl-4-yl 1-cyano-3-methylcyclohexanecarboxylate
4'-hexoxybiphenyl-4-yl 1-cyano-3-methylcyclohexanecarboxylate
4'-heptoxybiphenyl-4-yl 1-cyano-3-methylcyclohexanecarboxylate
4'-ethylbiphenyl-4-yl 1-cyano-3-ethylcyclohexanecarboxylate
4'-propylbiphenyl-4-yl 1-cyano-3-ethylcyclohexanecarboxylate
4'-butylbiphenyl-4-yl 1-cyano-3-ethylcyclohexanecarboxylate
4'-pentylbiphenyl-4-yl 1-cyano-3-ethylcyclohexanecarboxylate
4'-hexylbiphenyl-4-yl 1-cyano-3-ethylcyclohexanecarboxylate
4'-heptylbiphenyl-4-yl 1-cyano-3-ethylcyclohexanecarboxylate
4'-ethoxybiphenyl-4-yl 1-cyano-3-ethylcyclohexanecarboxylate
4'-propoxybiphenyl-4-yl 1-cyano-3-ethylcyclohexanecarboxylate
4'-butoxybiphenyl-4-yl 1-cyano-3-ethylcyclohexanecarboxylate
4'-pentoxybiphenyl-4-yl 1-cyano-3-ethylcyclohexanecarboxylate
4'-hexoxybiphenyl-4-yl 1-cyano-3-ethylcyclohexanecarboxylate
4'-heptoxybiphenyl-4-yl 1-cyano-3-ethylcyclohexanecarboxylate
4'-ethylbiphenyl-4-yl 1-cyano-3-chlorocyclohexanecarboxylate
4'-propylbiphenyl-4-yl 1-cyano-3-chlorocyclohexanecarboxylate
4'-butylbiphenyl-4-yl 1-cyano-3-chlorocyclohexanecarboxylate
4'-pentylbiphenyl-4-yl 1-cyano-3-chlorocyclohexanecarboxylate
4'-hexylbiphenyl-4-yl 1-cyano-3-chlorocyclohexanecarboxylate
4'-heptylbiphenyl-4-yl 1-cyano-3-chlorocyclohexanecarboxylate
4'-ethoxybiphenyl-4-yl 1-cyano-3-chlorocyclohexanecarboxylate
4'-propoxybiphenyl-4-yl 1-cyano-3-chlorocyclohexanecarboxylate
4'-butoxybiphenyl-4-yl 1-cyano-3-chlorocyclohexanecarboxylate
4'-pentoxybiphenyl-4-yl 1-cyano-3-chlorocyclohexanecarboxylate
4'-hexoxybiphenyl-4-yl 1-cyano-3-chlorocyclohexanecarboxylate
4'-heptoxybiphenyl-4-yl 1-cyano-3-chlorocyclohexanecarboxylate

EXAMPLE 2

A solution of lithium diisopropylamide (prepared from 3.3 g of diisopropylamine, 30 ml of THF and 19 ml of a 1.6 molar butyllithium solution in hexane) and then a solution of 9.7 g of 1-bromo-2-(4'-pentylbiphenyl-4-yl)ethane ethane in 30 ml of THF are added to a mixture of 3.1 g of 3-methylcyclohexanecarbonitrile and 30 ml of THF at −78°. Working up is carried out analogously to Example 1 to 1-(1-cyano-3-methylcyclohexyl)-2-(4'-pentylbiphenyl-4-yl)ethane, m.p. 73°, $[\alpha]_D^{20} = +1.1°$.

The following compounds are prepared analogously:

1-(1-cyano-3-methylcyclohexyl)-2-(4'-ethylbiphenyl-4-yl)ethane
1-(1-cyano-3-methylcyclohexyl)-2-(4'-propylbiphenyl-4-yl)ethane
1-(1-cyano-3-methylcyclohexyl)-2-(4'-butylbiphenyl-4-yl)ethane
1-(1-cyano-3-methylcyclohexyl)-2-(4'-hexylbiphenyl-4-yl)ethane
1-(1-cyano-3-methylcyclohexyl)-2-(4'-heptylbiphenyl-4-yl)ethane
1-(1-cyano-3-methylcyclohexyl)-2-(4'-ethoxybiphenyl-4-yl)ethane
1-(1-cyano-3-methylcyclohexyl)-2-(4'-propoxybiphenyl-4-yl)ethane
1-(1-cyano-3-methylcyclohexyl)-2-(4'-butoxybiphenyl-4-yl)ethane
1-(1-cyano-3-methylcyclohexyl)-2-(4'-pentoxybiphenyl-4-yl)ethane
1-(1-cyano-3-methylcyclohexyl)-2-(4'-hexoxybiphenyl-4-yl)ethane
1-(1-cyano-3-methylcyclohexyl)-2-(4'-heptoxybiphenyl-4-yl)ethane
1-(1-cyano-3-ethylcyclohexyl)-2-(4'-ethylbiphenyl-4-yl)ethane
1-(1-cyano-3-ethylcyclohexyl)-2-(4'-propylbiphenyl-4-yl)ethane
1-(1-cyano-3-ethylcyclohexyl)-2-(4'-butylbiphenyl-4-yl)ethane
1-(1-cyano-3-ethylcyclohexyl)-2-(4'-pentylbiphenyl-4-yl)ethane
1-(1-cyano-3-ethylcyclohexyl)-2-(4'-hexylbiphenyl-4-yl)ethane
1-(1-cyano-3-ethylcyclohexyl)-2-(4'-heptylbiphenyl-4-yl)ethane
1-(1-cyano-3-ethylcyclohexyl)-2-(4'-ethoxybiphenyl-4-yl)ethane
1-(1-cyano-3-ethylcyclohexyl)-2-(4'-propoxybiphenyl-4-yl)ethane
1-(1-cyano-3-ethylcyclohexyl)-2-(4'-butoxybiphenyl-4-yl)ethane
1-(1-cyano-3-ethylcyclohexyl)-2-(4'-pentoxybiphenyl-4-yl)ethane
1-(1-cyano-3-ethylcyclohexyl)-2-(4'-hexoxybiphenyl-4-yl)ethane
1-(1-cyano-3-ethylcyclohexyl)-2-(4'-heptoxybiphenyl-4-yl)ethane

EXAMPLE 3

1-(1-Cyano-3-methylcyclohexyl)-2-[4-(4-pentylcyclohexyl)phenyl-1-yl]-ethane, m.p. 92°, is obtained analogously to Example 3 by reaction of 1-bromo-2-[4-(4-pentylcyclohexyl)phenyl-1-yl]-ethane with 3-methylcyclohexanecarbonitrile.

The following compounds are prepared analogously:
1-(1-cyano-3-methylcyclohexyl)-2-[4-(4-ethylcyclohexyl)phenyl-1-yl]ethane
1-(1-cyano-3-methylcyclohexyl)-2-[4-(4-propylcyclohexyl)phenyl-1-yl]ethane
1-(1-cyano-3-methylcyclohexyl)-2-[4-(4-butylcyclohexyl)phenyl-1-yl]ethane
1-(1-cyano-3-methylcyclohexyl)-2-[4-(4-hexylcyclohexyl)phenyl-1-yl]ethane
1-(1-cyano-3-methylcyclohexyl)-2-[4-(4-heptylcyclohexyl)phenyl-1-yl]ethane

EXAMPLE A

A liquid crystal phase consisting of
24% of 4-(5-heptylpyrimidin-2-yl)-phenyl (p-pentylbenzyl)ether
24% of 4-(5-heptylpyrimidin-2-yl)-phenyl (p-heptylbenzyl)ether
18% of p-octoxyphenyl trans-4-heptylcyclohexanecarboxylate
15% of p-nonoxyphenyl trans-4-heptylcyclohexanecarboxylate
10% of p-hexoxyphenyl trans-4-pentylcyclohexanecarboxylate and
9% of 1-hydroxy-1-[r-1-cyano-cis-4-(trans-4-pentylcyclohexyl)cyclohexyl]-3-methylcyclohexane has C 0° $S_C^*$ 45° $S_A$ 54° Ch 61.5° I.

EXAMPLE B

A liquid crystal phase consisting of
3% of 2-p-hexyloxyphenyl-5-heptylpyrimidine,
3% of 2-p-heptyloxyphehyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
27% of 2-p-nonyloxyphenyl-5-nonylpyrimidine,
26% of r-1-cyano-1-butyl-cis-4-(4'-octyloxy-biphenyl-4-yl)cyclohexane,
13% of r-1-cyano-1-hexyl-cis-4-(4'-heptylbiphenyl-4-yl)cyclohexane,
5% of r-1-cyano-cis-1-(4-pentylcyclohexyl)-trans-4-(4-pentylcyclohexyl)cyclohexane and
10% of 4'-hexylbiphenyl-4-yl 1-cyano-3-methylcyclohexanecarboxylate has C $-9°$ $C_C^*$ 61° $S_A$ 69° Ch 81° I and a spontaneous polarization $P_S$ of 7 nC/cm$^2$.

EXAMPLE C

A liquid crystal phase consisting of
10% of r-1-cyano-1-pentyl-cis-4-(4'-butylbiphenyl-4-yl)cyclohexane,
45% of r-4-cyano-1-pentyl-cis-4-(4'-octylbiphenyl-4-yl)cyclohexane,
42% of r-1-cyano-1-butyl-cis-4-(4'-octyloxybiphenyl-4-yl)cyclohexane and
5% of 1-hydroxy-1-[r-1-cyano-cis-4-(trans-4-pentylcyclohexyl)cyclohexyl]-3-methylcyclohexane has C 30° $S_C^*$ 65° $S_A$ 90° Ch 125 I and $P_S=1$ nC/cm$^2$.

EXAMPLE D

A liquid crystal phase consisting of
2% of 2-p-hexyloxyphenyl-5-heptylpyrimidine,
7% of 2-p-hexyloxyphenyl-5-nonylpyrimidine,
2% of 2-p-heptyloxyphenyl-5-heptylpyrimidine,
2% of 2-p-octyloxyphenyl-5-heptylpyrimidine,
25% of 2-p-nonyloxyphenyl-5-nonylpyrimidine,
2% of 2-p-nonyloxyphenyl-5-heptylpyrimidine,
30% of r-1-cyano-1-octyl-cis-4-(4'-octyloxybiphenyl-4-yl)cyclohexane,
5% of r-1-cyano-1-heptyl-cis-4-(4'-hexylbiphenyl-4-yl)cyclohexane,
14% of optically active r-1-cyano-1-(2-methylbutyl)-cis-4-(4'-heptyloxybiphenyl-4-yl)-cyclohexane and
11% of optically active 1-(1-cyano-3-methylcyclohexyl)2-(4'-pentylbiphenyl-4-yl)-ethane shows C$< -30°$ $S_C^*$ 65 $S_A$ 71 Ch 87 I and a spontaneous polarization $P_S$ of +32.7 nC/cm$^2$.

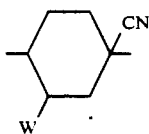

We claim:

1. An optically active compound of the formula Ii $$R^1\text{-A-}Z^1\text{-A}^2\text{-A}^3\text{-R}^3 \qquad (Ii)$$

wherein
$R^1$ is H or alkyl of 1-12 C atoms;
A is 1,4-cyclohexylene containing an asymmetric carbon atom and substituted in the 2-, or 3 position by alkyl of 1-10 C atoms and in the 1- or 4-position by nitrile;
$A^2$ and $A^3$ are each independently (a) 1,4-cyclohexylene; or (b) 1,4-phenylene which is unsubstituted or substituted by one or two F atoms, and wherein in each case one or two CH groups can be replaced by N;
$Z^1$ is —CO—O—, —O—CO—, —CH$_2$CH$_2$—, —OCH$_2$—, —CH$_2$O— or a single bond; and
$R^3$ is F, Cl, Br, Cn or alkyl of 1-12 C atoms, wherein one or two nonadjacent CH$_2$ groups can also be replaced by O atoms and/or —CO—O—groups and/or —CH=CH—groups.

2. An optically active compound of claim 1, of the formulae Ii1 to Ii4:

$$R^1\text{-A-}Z^1\text{-Cy-Cy-}R^3 \qquad (Ii1)$$

$$R^1\text{-A-}Z^1\text{-Ph-Cy-}R^3 \qquad (Ii2)$$

$$R^1\text{-A-}Z^1\text{-Cy-Ph-}R^3 \qquad (Ii3)$$

or
$$R^1\text{-A-}Z^1\text{-Ph-Ph-}R^3 \qquad (Ii4)$$

wherein Cy is a 1,4-cyclohexylene group and pH is a 1,4-phenylene group wherein one or two CH-groups can be replaced by N.

3. An optically active compound of claim 2, wherein $Z^1$ is —O—CO—, —CO—O— or —CH$_2$CH$_2$—.

4. An optically active compound of claim 1, wherein $R^3$ is alkyl or oxaalkyl.

5. An optically active compound of claim 1, wherein each of $A^2$ and $A^3$ independently is trans-1,4-cyclohexylene, 1,4-phenylene or pyrimidine-2,5-diyl.

6. An optically active compound of claim 1, wherein A is of formula (A)

wherein W is alkyl of 1 to 10 C atoms.

7. An optically active compounds of claim 6, wherein W is CH$_3$.

8. An optically active compound of claim 1, wherein $R^1$ is H.

9. An optically active compound of claim 4 wherein $R^3$ is alkyl or alkoxy.

10. A compound according to claim 1, wherein A is substituted in the ortho-position, relative to said nitrile, by said alkyl.

11. A compound according to claim 1, wherein A is substituted in the meta-position, relative to said nitrile, by said alkyl.

12. A compound according to claim 1, wherein A is substituted in the same position by both said nitrile and $R^1$.

13. A compound according to claim, wherein group A is substituted in the para-position, relative to $R^1$, by said nitrile.

14. A compound according to claim 12, wherein A is substituted by said alkyl in the 2-position.

15. A compound according to claim 12, wherein A is substituted by said alkyl in the 3-position.

16. A compound according to claim 13, wherein A is substituted by said alkyl in the 2-position.

17. A compound according to claim 13, wherein A is substituted by said alkyl in the 3-position.

18. A chiral tilted smectic liquid crystal medium containing at least two liquid crystal components, wherein at least one compound is an optically active compound of the Formula Ii $$R^1\text{-A-}Z^1\text{-A}^2\text{-A}^3\text{-R}^3 \qquad \text{(Ii)}$$

wherein $R^1$ is H or alkyl or 1-12 C atoms;

A is 1,4-cyclohexylene containing an asymmetric carbon atom and substituted in the 2-, or 3 position by alkyl of 1-10 C atoms and in the 1- or 4-position by nitrile;

$A^2$ and $A^3$ are each independently (a) 1,4-cyclohexylene or (b) 1,4-phenylene which is unsubstituted or substituted by one or two F atoms and wherein, in each case, one or two CH groups can be replaced by N;

$Z^1$ is —CO—O—, —O—CO—, —CH$_2$CH$_2$—, —OCH$_2$—, —CH$_2$O—, or a single bond; and $R^3$ is F, Cl, Br, CN, or alkyl or 1-12 C atoms, wherein one or two nonadjacent CH$_2$ groups can also be replaced by O atoms and/or —CO—O— groups and/or —CH=CH— groups.

19. An electrooptical display element, comprising a liquid crystal dielectric, wherein the dielectric is a medium of claim 18.

20. A medium according to claim 18, wherein ring A is a structure of the formula